United States Patent [19]

Schlueter et al.

[11] Patent Number: 5,208,195
[45] Date of Patent: May 4, 1993

[54] PROCESS FOR THE PREPARATION OF A CATALYST FOR THE HYDRATION OF OLEFINS TO GIVE ALCOHOLS

[75] Inventors: Dietrich Schlueter, Sobernheim; Franz-Josef Baumeister, Recklinghausen; Klaus-Peter Schubert, Herne, all of Fed. Rep. of Germany

[73] Assignee: Huels Aktiengesellschaft, Marl, Fed. Rep. of Germany

[21] Appl. No.: 845,155

[22] Filed: Mar. 3, 1992

[30] Foreign Application Priority Data

Mar. 13, 1991 [DE] Fed. Rep. of Germany ....... 4107973

[51] Int. Cl.$^5$ .......................... B01J 21/16; B01J 37/00
[52] U.S. Cl. ......................................... 502/63; 502/81; 502/84
[58] Field of Search ................................... 502/81–84, 502/63

[56] References Cited

U.S. PATENT DOCUMENTS

| | | | |
|---|---|---|---|
| 2,713,560 | 7/1955 | Morrell | 502/84 |
| 2,862,875 | 12/1958 | Morrell | 502/84 |
| 3,311,568 | 3/1967 | Klimenko et al. | 502/81 |
| 4,808,559 | 2/1989 | Sommer et al. | 502/63 |

FOREIGN PATENT DOCUMENTS 1371905  10/1974  United Kingdom ................ 502/81

*Primary Examiner*—Carl F. Dees
*Attorney, Agent, or Firm*—Oblon, Spivak, McClelland, Maier & Neustadt

[57] ABSTRACT

A catalyst of a phosphoric acid treated carrier formed from clay minerals and silica gel for the hydration of a $C_{2-3}$ olefin to an alcohol is prepared by acid treating an essentially montmorillonite-containing clay contaminated with not more than 3% of extraneous materials until an acid treated clay is obtained having a 10–20% by weight $Al_2O_3$ content and a specific surface area of 200 to 400 m$^2$/g, adding from 20 to 40 parts by weight of finely particulate silica gel having a particle size distribution of between 30 and 60×10$^{-6}$ m, a pore volume of 0.9 to 1.7 ml/g and a specific surface are of 200 to 500 m$^2$/g and from 1.5 to 2.5 parts by weight of titanium dioxide, each based on total dry substance, to said acid treated clay, shaping the acid treated material to a total water content of 40 to 60% by compression, calcining the shaped material at 500° to 900° C., in a second stage, acid treating the calcined material with acid until it has an $Al_2O_3$ content of 1 to 4% by weight and has a specific surface area of 180 to 250 m$^2$/g and a pore volume of between 0.8 to 1.5 ml/g, and impregnating the acid treated material with phosphoric acid.

9 Claims, No Drawings

PROCESS FOR THE PREPARATION OF A CATALYST FOR THE HYDRATION OF OLEFINS TO GIVE ALCOHOLS

BACKGROUND OF THE INVENTION

1. Field of the Invention

The present invention relates to an improved catalyst for the hydration of olefins with steam to give alcohol products.

2. Description of the Background

It is known that olefins can be reacted with steam in the gas phase at elevated pressures to give alcohols. Such processes have become particularly important industrially for the production of ethanol from ethylene and isopropyl alcohol from propylene. The synthesis of these alcohols is carried out in the presence of a catalyst, the catalyst generally used being phosphoric acid, which is applied to carriers. Known carriers are either those based on pure silica, such as, for example, kieselguhr or silica gel (U.S. Pat. No. 2,579,601) or those based on silica with a higher or lower alumina content, such as, for example, calcined diatomaceous earth, the structure of which is held together by clay or clay-containing substances (German Patent 2,722, 616 and U.S. Pat. No. 3,311,568).

In the case of the carriers on pure silica, the strength over a prolonged time-on-stream presents problems. Although the alumina-containing materials are distinguished by better mechanical strength, when they have an excessively high alumina content, they have the disadvantage that the alumina is dissolved away during the reaction by the action of the phosphoric acid.

German patent 1,156,772 describes a process for the preparation of an alumina-containing carrier for the phosphoric acid used as a catalyst in the hydration of olefins, in which process catalyst moldings of mineral aluminum silicates are treated with a mineral acid in such a way that the alumina content is preferably reduced to between 1 and 5 per cent by weight. This material generally has both the required mechanical strength and a sufficiently low residual aluminum content to avoid removal by dissolution. On the other hand, when commercial catalyst elements are used for the preparation of catalyst carriers for the hydration of olefins, it has been observed that, without preselection of the raw material, very different catalyst activities are found.

Finally, it has been possible to develop, also based on coarse-pore silica gels, carriers for phosphoric acid having high hydration activity and sufficient mechanical strength (German Patent 2,525,705 and 2,719,055).

However, the remaining disadvantage of these carriers based on amorphous silica is that the amorphous silica partially crystallizes during prolonged use under conditions of the hydration reaction, which is associated with a sharp reduction in the specific surface area and hence in the catalytic activity, in an irreversible manner, and with a decrease in the mechanical strength.

A further disadvantage of all hydration catalysts used to date, which are based on phosphoric acid on a silicate carrier, is the slow decrease exhibited in their activity as a result of the discharge of phosphoric acid, which, during continuous operation, must be constantly neutralized with an alkali in order to avoid corrosion effects of the acidic crude alcohols on downstream apparatuses. By continuously spraying in phosphoric acid according to German Patent 2,658,946 in an amount which corresponds to the amount of phosphoric acid discharged, it has been possible substantially to avoid the continuous loss of activity and hence considerably prolonging catalyst life; however, this involves setting corresponding requirements for the life of the carrier, so that it is not possible to use such carriers in which, under reaction conditions, crystallization occurs with a reduction in the catalytic activity in an irreversible manner and the mechanical strength decreases over the course of time.

As indicated in German Patent 2,908,491, a carrier for a hydration catalyst of constantly high catalytic activity can be obtained from clay minerals when, by a careful choice of the raw material, care is taken to ensure that the material consists to a large extent of montmorillonite, which results in a large surface area and a large absorption volume after shaping, leaching and impregnation. The resulting catalysts or catalyst carriers of montmorillonite-containing clay have a higher activity than those prepared from molded catalysts based on mineral aluminum silicates of different origin, i.e. about 105 to 110 g of ethanol or about 300 g of isopropyl alcohol are obtained per hour per liter of catalyst bed. However, this increased activity can only be maintained over a relatively long period, if the discharged phosphoric acid, which amounts to about 0.07 g per hour and per liter of catalyst bed in the case of ethanol and about 0.01 g per hour and per liter of catalyst bed in the case of isopropyl alcohol, is compensated by the continuous addition of the same amount of acid. This discharged acid must moreover be neutralized with an alkali. The mechanical strength of the catalysts is of the order of magnitude of 70 to 90 Newton/sphere, which is sufficient for the loading of the conventional reactors. Thus, once a catalyst having an adequate life and long-term strength has been found and the discharge of phosphoric acid has been suppressed to a satisfactory value, the carriers consisting predominantly of silica gel remained superior to the carriers prepared from montmorillonite only with regard to their initial activity. Thus, according to German Patent 2,722,616, up to 144 g of ethanol per hour and per liter of catalyst bed are produced, but only 115 g of isopropyl alcohol per hour and per liter of catalyst bed. U.S. Pat. No. 3,311,568 describes a substantially higher catalyst activity, namely 240 g of ethanol per hour and per liter of catalyst bed, phosphoric acid being metered in every 24 hours and in general the activity being observed only over 1500 hours, i.e. about two months. It is reported that the strength increases with a higher content of bentonite, and the mixing of 3 to 5% of bentonite with the diatomaceous earth prior to sintering is described.

Finally, according to German Offenlegungsschrift 3,709,401, it was found that the good catalyst properties according to German Patent 2,908,491 and German Patent 2,929,919 with regard to long-term strength and good retention of the phosphoric acid are maintained in terms of the amount of alcohol produced per unit time and catalyst volume, can be considerably increased, this activity remaining virtually unchanged over a period of six months, if 20 to 40 per cent by weight, based on the total dry substance, of a fine-particled silica gel are added to the clay treated with acid in the first stage and having a high montmorillonite content, prior to molding for calcination, and the surface area and pore volume of the finished catalyst carrier is thus increased. Since the montmorillonite carrier alone in the leached state prior to impregnation with phosphoric acid has a specific surface area of only 150 to 160 m$^2$/g and a pore volume of about 0.7 ml/g, it is not difficult to see that, as a result of the addition of, for example, 30% of silica gel (specific surface area about 350 m$^2$/g), the specific surface area increases only linearly to 180-200 m$^2$/g, whereas the pore volume (addition: silica gel 1.0 to 1.2 ml/g) increases disproportionately to 0.95-1.0 ml/g, which is critical for the increase in activity. The pore diameters of the finished carrier prior to impregnation with phosphoric acid are between 1 and $20 \cdot 10^{-9}$ m and the maximum of the frequency distribution is about $5 \cdot 10^{-9}$ m. In the process according to German Patent 3,709,401, it has been found that an increase in the compressive strength of the spheres, which occurs in the case of the natural product montmorillonite on subsequent calcination, is transferred to the mixed carrier even under process conditions, whereas pure silica gel always suffers a loss of strength under process conditions. A need therefore continues to exist for an olefin hydration catalyst carrier of improved strength.

SUMMARY OF THE INVENTION

Accordingly, one object of the present invention is to provide a mixed catalyst of improved properties, in particular with regard to strength.

Briefly, this object and other objects of the present invention as hereinafter will become more readily apparent can be attained in a process for the preparation of a catalyst of a phosphoric acid treated carrier prepared from clay materials and silica gel for the production of an alcohol by the hydration of an olefin having 2 to 3 C atoms by acid treating an essentially montmorillonite-containing clay contaminated with not more than 3% of extraneous materials until an acid treated clay is obtained having a 10-20% by weight Al$_2$O$_3$ content and a specific surface area of 200 to 400 m$^2$/g, adding from 20 to 40 parts by weight of finely particulate silica gel having a particle size distribution of between 30 and $60 \times 10^{-6}$ m, a pore volume of 0.9 to 1.7 ml/g and a specific surface titanium dioxide, each based on total dry substance, to said acid treated clay, shaping the acid treated material to a total water content of 40 to 60% by compression, calcining the shaped material at 500° to 900° C., in a second stage, acid treating the calcined material with acid until it has an Al$_2$O$_3$ content of 1 to 4% by weight and has a specific surface area of 180 to 250 m$^2$/g and a pore volume of between 0.8 to 1.5 ml/g, and impregnating the acid treated material with phosphoric acid.

DETAILED DESCRIPTION OF THE PREFERRED EMBODIMENTS

It has now been found, surprisingly, that an increase in the compressive strength of the catalyst spheres occurs as a result of the addition of finely divided TiO$_2$ in certain amounts to the montmorillonite/silica gel carrier.

In the process of the invention, an essentially montmorillonite-containing clay, contaminated with not more than 3% of other materials such as quartz, feldspar and mica and optionally containing up to 0.5% of K$_2$O is acid treated with the likes of HCl to a 10-20% by weight, preferably 13-18% by weight, Al$_2$O$_3$ content. The acid treated material has a specific surface area of 200 to 400 m$^2$/g, preferably 240 to 300 m$^2$/g. The acid treated clay is then mixed with 20 to 40 parts by weight of finely divided silica gel and 1.5 to 2.5 parts by weight of titanium dioxide, each based on the total dry substances. The silica gel has a particle size distribution of between 30 and $60 \times 10^{-6}$ m, a pore volume of 0.9 to 1.7 ml/g, preferably 1 to 1.2 mg/g, and a specific surface area of 200 to 500 m$^2$/g, preferably 380 to 400 m$^2$/g.

The mixture is optionally shaped and calcined. Shaping is achieved by compression to a total water content of 40 to 60% and then the shaped material is calcined at 500° to 900° C.

The shaped and calcined carrier is then acid treated in a second stage to an Al$_2$O$_3$ content of 1 to 4% by weight, preferably 1 to 2% by weight, a specific surface area of 180 to 250 m$^2$/g, preferably 200 to 220 m$^2$/g, and a pore volume of between 0.8 and 1.5 ml/g, preferably 0.9 to 1 ml/g. The catalyst is completed by adding phosphoric acid to the carrier.

The amounts of titanium dioxide added to the carrier materials should not be less than or more than 1.5 to 2.5 parts. A mixed carrier of 2 parts of titanium dioxide, 70 parts of bentonite and 30 parts of silica gel is preferred.

Hydrothermal tests with a carrier laden with 40% H$_3$PO$_4$ and containing 5 parts of titanium dioxide showed a reduction in the pore volume (PV) of the carrier from 0.98 ml/g to 0.75 ml/g with a disproportionate increase in strength from 80 Newton to 150 Newton/sphere under thermal stress at 250° C. and 70 bar and with a nitrogen/water ratio of 2.5 : 1. A reduction in the PV always leads to losses of activity.

Added amounts of only about 1 part of titanium dioxide showed scarcely any increase in the initial strength.

Hydrothermal tests with a mixed carrier of 2 parts of titanium dioxide, 30 parts of silica gel and 70 parts of bentonite showed scarcely any change in the total pore volume, which remained constant, whereas the initial strength increased from 80 Newton to 120 Newton/sphere.

The characteristics of the titanium dioxide with regard to its particle size should preferably be about $10^{-6}$ m in order to ensure uniform distribution in the end product when the three components are mixed. The specific surface area should preferably have values in a range of 5-15 m$^2$/g, particularly preferably 10 m$^2$/g, and the analytical purity should be greater than 99.5% by weight, determined cerimetrically, in order to rule out secondary reactions.

Having now generally described this invention, a further understanding can be obtained by reference to certain specific examples which are provided herein for purposes of illustration only and are not intended to be limiting unless otherwise specified.

EXAMPLE 1

A milled natural raw clay, which was chosen on the basis of a laboratory test so that, when treated for one hour with 20% strength hydrochloric acid at 82° C., not more than 5 g of K$_2$O per kg of dry substance used are extracted, was heated for one hour with 20% strength hydrochloric acid at 82° C., the amount of acid being such that there were 8.4 mol of HCl per 1 kg of clay. The clay was washed acid-free and dried. A material having a residual aluminum content of 16 per cent by weight and a specific surface area of 300 m$^2$/g was obtained.

30 parts of fine-particled silica gel from W. R. Grace, Worms, having a particle size distribution mainly between 30 and $60 \cdot 10^{-6}$ m, a pore volume of 1.1 ml/g and a specific surface area of 410 m$^2$/g, and 2 parts of titanium dioxide having a particle size of about $10^{-6}$ m and a specific surface area of 9 m²/g were added to 70 parts of this dried material, the water content was increased to 50% and the material was then compressed to give spheres of 5 mm diameter. Compaction was effected by heating for 5 hours at 800° C.

The catalyst spheres thus obtained were heated twice, for one hour in each case, with 20% strength hydrochloric acid at 100° to 110° C. and were washed acid-free with water. After drying at about 110° to 120° C., the alumina content of the spheres was determined as 1.4 per cent by weight and the titanium dioxide content of the spheres as 1.8% by weight. The specific surface area was 185 m²/g and the pore volume 0.96 ml/g. The spheres were then impregnated with 60% strength by weight phosphoric acid, which was allowed to act for two hours, and were then dried at about 110° to 120° C.. The $H_3PO_4$ content of the spheres treated in this manner was 45.1% by weight; the mean compressive strength was 80 Newton/sphere.

When the hydration catalyst prepared in this manner was used for the synthesis of ethanol from ethylene and water in the gas phase at a temperature of 235° C. and a pressure of 70 bar, a catalyst yield of 160 g of ethanol per hour and per liter of catalyst bed could be obtained. This value was still virtually unchanged after the plant had operated for six months. Discharge of phosphoric acid under reaction conditions was 0.07 g per hour per liter of catalyst bed.

When the mixed carrier containing 2 parts of titanium dioxide was removed, it was found that the compressive strength of the spheres had increased to 120 Newton/sphere and that the strength was still about 110 Newton/sphere even after extraction with water. The pore volume decreased slightly to 0.95 ml/g, and the specific surface area had decreased to about 30 m²/g. At the same time there was a shift in pore size from a diameter of $10^{-8}$ m to $10^{-6}$ m, which is normal in the synthesis for the corresponding operating time.

EXAMPLE 2

A milled natural raw clay, which was chosen on the basis of a laboratory test so that, when treated for one hour with 20% strength hydrochloric acid at 82° C., not more than 5 g of $K_2O$ per kg of dry substance used are extracted, was heated for one hour with 20% strength hydrochloric acid at 82° C., the amount of acid being such that there were 8.4 mol of HCl per one kg of clay, and was washed acid-free and dried. A material having a residual aluminum content of 16 per cent by weight and a specific surface area of 300 m²/g was obtained.

30 parts of fine-particled silica gel from W. R. Grace, Worms, having a particle size distribution mainly between 30 and 60·$10^{-6}$ m, a pore volume of 1.1 ml/g and a specific surface area of 410 m²/g were added to 70 parts of this dried material, and 2 parts of titanium dioxide having a particle size distribution around $10^{-6}$ m and a specific surface area of 9 m²/g were then also added to these 100 parts. After the water content had been increased to 50%, based on the total amount, the materials were then compressed to give spheres of 5 mm diameter. Compaction was effected by heating for 5 hours at 800° C. The catalyst spheres thus obtained were heated twice, for one hour in each case, with 20% strength hydrochloric acid at 100° to 110° C. and were washed acid-free with water. After drying at about 110° to 120° C., the alumina content in the spheres was determined as 1.4 per cent by weight and the titanium dioxide content of the spheres as 1.85% by weight. The specific surface area was 200 m²/g and the pore volume 0.94 ml/g. The spheres were then flooded with 40% strength by weight phosphoric acid, which acted for two hours, after which drying was carried out again at about 110° to 120° C. The spheres treated in this manner had an $H_3PO_4$ content of 32 per cent by weight. The mean compressive strength was 80 Newton/sphere.

When the hydration catalyst prepared in this manner was used for the synthesis of isopropyl alcohol from propylene and water in the gas phase at a temperature of 186° C. and a pressure of 38 bar, a catalyst yield of 360 g of isopropyl alcohol per hour per liter of catalyst bed could be obtained. This value had not changed after the plant had operated for six months. Discharge of phosphoric acid under reaction conditions was 0.005 g per hour per liter of catalyst bed. Here, too, when the mixed carrier containing titanium dioxide was removed, it was found that the compressive strength of the carrier had increased from 80 Newton to 100 Newton/sphere during the hydration process under the temperature conditions, which, however, were relatively low. After removal of the phosphoric acid, the pore volume was found to have remained virtually constant at 0.93 ml/g, whereas the specific surface area had decreased to about 40 m²/g, which however had no adverse effect on the activity during reuse when the carrier was reimpregnated with phosphoric acid.

EXAMPLE 3 (Comparison)

A milled natural raw clay, which was chosen on the basis of a laboratory test so that, when treated for one hour with 20% strength hydrochloric acid at 82° C., not more than 5 g of $K_2O$ per kg of dry substance used are extracted, was heated for one hour with 20% strength hydrochloric acid at 82° C., the amount of acid being such that there were 8.4 mol of HCl per one kg of clay, and was washed acid-free and dried. A material having a residual aluminum content of 16 per cent by and a specific surface area of 300 m²/g was obtained 30 parts of fine-particled silica gel from W. R. Grace, Worms, having a particle size distribution mainly between 30 and 60·$10^{-6}$ m, a pore volume of 1.1 ml/g and a specific surface area of 410 m²/g were added to 70 parts of this dried material, the total water content was increased to 50% and the material was then compressed to give spheres of 5 mm diameter. Compaction was effected by heating for 5 hours at 800° C. The catalyst spheres thus obtained were heated twice, for one hour in each case, with 20% strength hydrochloric acid at 100° to 110° C. and were washed acid-free with water. After drying at about 110° to 120° C., the alumina content of the spheres was determined as 1.5 per cent by weight. The specific surface area was 210 m²/g and the pore volume was 0.95 ml/g. The spheres were then flooded with 60% strength by weight phosphoric acid, which acted for two hours, after which drying was carried out again at about 110° to 120° C. The spheres treated in this manner had an $H_3PO_4$ content of 44.8 per cent by weight. The mean compressive strength was 70 Newton/sphere.

When the hydration catalyst prepared in this manner was used for the synthesis of ethanol from ethylene and water in the gas phase at a temperature of 235° C. and a pressure of 70 bar, a catalyst yield of 160 g of ethanol per hour per liter of catalyst bed could be obtained. This value was still virtually unchanged after the plant had operated for six months. Discharge of phosphoric acid under reaction conditions was 0.07 g per hour per liter of catalyst bed. When the mixed carrier was removed, it was found that the compressive strength of the spheres had increased from 70 Newton to 90 Newton/sphere under process conditions, a feature which we have previously observed only in the case of pure montmorillonite carriers.

In the case of a carrier without added silica gel, the specific surface area was 160 $m^2/g$ prior to impregnation with phosphoric acid, and the pore volume was 0.7 ml/g. Under the same reaction conditions, namely 70 bar and 235° C., an amount of only 135 g of ethanol was obtained per hour per liter of catalyst bed with this carrier in the synthesis of ethanol from ethylene and water.

Having now fully described the invention, it will be apparent to one of ordinary skill in the art that many changes and modifications can be made thereto without departing from the spirit or scope of the invention as set forth herein.

WHAT IS CLAIMED AS NEW AND DESIRED TO BE SECURED BY LETTERS PATENT OF THE UNITED STATES IS:

1. A process for the preparation of a catalyst of a phosphoric acid treated carrier prepared from clay minerals and silica gel for the production of an alcohol by the hydration of $C_{2-3}$ olefin which comprise:

acid treating an essentially montmorillonite-containing clay contaminated with not more than 3% of extraneous materials until an acid treated clay is obtained having a 10–20% by weight $Al_2O_3$ content and a specific surface area of 200 to 400 $m^2/g$;

adding from 20 to 40 parts by weight of finely particulate silica gel having a particle size distribution of between 30 and $60 \times 10^{-6}$ m, a pore volume of 0.9 to 1.7 ml/g and a specific surface are of 200 to 500 $m^2/g$ and from 1.5 to 2.5 parts by weight of titanium dioxide, each based on total dry substance, to said acid treated clay;

shaping the acid treated material to a total water content of 40 to 60% by compression;

calcining the shaped material at 500° to 900°C.;

in a second stage, acid treating the calcined material with acid until it has an $Al_2O_3$ content of 1 to 4% by weight and has a specific surface area of 180 to 250 $m^2/g$ and a pore volume of between 0.8 to 1.5 ml/g; and impregnating the acid treated material with phosphoric acid.

2. The process according to claim 1, wherein the mixed carrier consists of 70 parts of bentonite, 30 parts of silica gel and 2 parts of titanium dioxide.

3. The process of claim 1, wherein the materials in the clay are selected from the group consisting of quartz, feldspar and mica and up to 0.5% of $K_2O$.

4. The process of claim 1, wherein the clay is acid treated to 13–18% by weight of $Al_2O_3$, the clay having a specific surface area of 240 to 300 $m^2/g$.

5. The process of claim 1, wherein as a result of the second acid treatment, the clay has an $Al_2O_3$ content of 1 to 2% by weight and has a specific surface area of 200 to 220 $m^2/g$ and a pore volume of between 0.9 to 1 ml/g.

6. The process of claim 1, wherein the silica gel has a pore volume of 1 to 1.2 ml/g and a specific surface area of 380 to 400 $m^2/g$.

7. The process of claim 1, wherein the titanium oxide has a particle size of about $10^{-6}$ m and specific surface area of 5–15 $m^2/g$ and an analytical purity of greater than 99.5% by weight.

8. The process of claim 7, wherein said surface area is 10 $m^2/g$.

9. The process of claim 1, wherein said montmorillonite clay contains up to 0.5% of $K_2O$.

* * * * *